(12) United States Patent
Tahara et al.

(10) Patent No.: US 9,011,745 B2
(45) Date of Patent: Apr. 21, 2015

(54) METHOD FOR MANUFACTURING A MEDICAL TUBE

(75) Inventors: Hitoshi Tahara, Settsu (JP); Akitoshi Sakata, Settsu (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 13/702,896

(22) PCT Filed: Jun. 7, 2011

(86) PCT No.: PCT/JP2011/063051
§ 371 (c)(1),
(2), (4) Date: Dec. 7, 2012

(87) PCT Pub. No.: WO2011/155491
PCT Pub. Date: Dec. 15, 2011

(65) Prior Publication Data
US 2013/0090632 A1    Apr. 11, 2013

(30) Foreign Application Priority Data
Jun. 10, 2010 (JP) ................. 2010-133440

(51) Int. Cl.
*B29C 65/00* (2006.01)
*A61M 25/00* (2006.01)

(52) U.S. Cl.
CPC ....... *A61M 25/0012* (2013.01); *A61M 25/0009* (2013.01); *A61M 25/005* (2013.01)

(58) Field of Classification Search
None
See application file for complete search history.

(56) References Cited

U.S. PATENT DOCUMENTS 5,951,539 A * 9/1999 Nita et al. ............. 604/526
7,001,420 B2 * 2/2006 Speck et al. ............ 623/1.11
7,149,585 B2 * 12/2006 Wessman et al. .......... 607/116

FOREIGN PATENT DOCUMENTS

| JP | 4-183478 A | 6/1992 |
|----|------------|--------|
| JP | 2002-535049 A | 10/2002 |
| JP | 2007-151913 A | 6/2007 |
| JP | 2009-207737 A | 9/2009 |
| WO | WO 00/43061 A1 | 7/2000 |
| WO | WO 2009/126747 A1 | 10/2009 |

OTHER PUBLICATIONS

International Search Report mailed on Aug. 16, 2011, issued in PCT/JP2011/063051.

* cited by examiner

*Primary Examiner* — Edmund H. Lee
(74) *Attorney, Agent, or Firm* — Birch Stewart Kolasch & Birch, LLP

(57) ABSTRACT

It is an object to stably provide a thin-walled flexible medical tube having excellent kink resistance and tensile strength by a simple manufacturing method. The object is achieved by a method for manufacturing a medical tube that includes a coil layer on an inside of an outer layer tube made of a resin, and the method includes inserting the coil layer into the outer layer tube and heating the outer layer tube at a molding temperature lower than a melting point of the outer layer tube, thereby bringing the outer layer tube into contact with the coil layer to slidably fix the outer layer tube onto the coil layer.

18 Claims, 2 Drawing Sheets

METHOD FOR MANUFACTURING A MEDICAL TUBE

TECHNICAL FIELD

The present invention relates to a thin-walled flexible medical tube having excellent kink resistance and tensile strength and a method for manufacturing the medical tube.

BACKGROUND ART

There is a conventionally carried out medical practice in which a catheter is percutaneously inserted into a blood vessel and is introduced to an organ such as the brain, the heart, and the abdomen, thereby administrating and injecting, for example, a therapeutic agent, an embolic material, or a contrast medium, delivering, for example, an endoscope, another catheter, or a guide wire, or aspirating, for example, a blood clot. With the recent progress in medicine, for example, the treatment in a thinner peripheral blood vessel and a minimally invasive treatment using a catheter having a smaller outer diameter have been being carried out, and such a treatment requires a catheter having a smaller diameter but having higher performance than ever before. Examples of the performance of a catheter include pushability of reliably transferring a pushing force from an operator to the leading end of a catheter and reachability to a thin and bent peripheral blood vessel. For the injection of a medicinal agent, the aspiration of a blood clot, and the delivery performance of an endoscope or another catheter, the inner diameter of a catheter is very important. In addition, in order to carry out a minimally invasive treatment, the outer diameter is also required to be reduced, and hence an extremely thin-walled tube is required. Until now, it has been very difficult to ensure that such a thin-walled tube has kink resistance of preventing a catheter from being bent even at a bent part or a curved part of a blood vessel, inner cavity retention performance when a catheter is highly bent, and tensile strength for preventing a catheter from being easily broken when, for example, the catheter is caught in the body.

Conventionally, as a tube having excellent kink resistance and excellent inner cavity retention performance when the tube is highly bent, a resin tube including a coil structure as a reinforcement layer has been studied. The coil structure is extremely excellent in the kink resistance and the inner cavity retention performance when a tube is highly bent but is inferior in the tensile strength. Thus, in order to ensure the tensile strength of a tube using the coil structure, a resin tube is required to have a much heavier wall thickness or to include a resin having high rigidity. However, a heavy-walled tube has an increased outer diameter or a reduced inner diameter, and this raises problems in which, for example, such a tube cannot be inserted into a thinner peripheral blood vessel, cannot achieve a minimally invasive treatment, and causes the reduction of the injection performance, the aspiration performance, and the delivery performance. A tube including a resin having high rigidity generally has low toughness, and this raises problems in which the resin layer cracks when the tube is highly bent, thereby reducing the kink resistance and the tensile strength. Hence, such a tube cannot be safely used.

As a method for improving the tensile strength of a tube including a coil structure as a reinforcement layer, a method using an axial member in the longitudinal direction of a catheter is disclosed (Patent Document 1). Patent Document 1 describes an intravascular catheter that further includes an axial member extending along a reinforcement layer including a braid. It is described that the combination of the axial member can prevent a shaft from being elongated. In the structure, the axial member is not fixed to any polymer layer adjacent to the braid. Though the method surely suppresses the elongation in the axial direction, the strength of a wire of the axial member is required to be increased against a higher tensile force, and a catheter obtained by the method may cause anisotropic flexural rigidity. In addition, an embodiment in Patent Document 1 describes that, in the manufacturing process, a composite subassembly including the axial member, the braid, the polymer layer, and others is heated, thereby fusing and compressing the members to each other.

Another disclosed method is a method of providing a braided structure on the outside of a coil structure (Patent Document 2). In Patent Document 2, a flat square braided part made of metal is provided on the outside of a flat plate-shaped tightly wound coil made of metal, and a resin covering layer is further provided on the outside of the flat square braided part. The tube intends to satisfy both the compressive force resistance due to the coil structure when the tube is bent and the tensile force resistance due to the braided structure. However, when the thickness or the width of a wire constituting the braid is increased against high tensile force, the compressive force resistance when the tube is bent, obtained by the coil structure is reduced. Therefore, such a tube is difficult to be applied to the leading end of a catheter that is required to have flexibility and high tensile force.

These techniques have structures requiring a reinforcement layer in addition to the coil layer and the resin layer and hence are absolutely impossible to be applied to a thin-walled tube.

CITATION LIST

Patent Literatures

Patent Document 1: JP-A No. 2002-535049
Patent Document 2: JP-A No. 4-183478

SUMMARY OF INVENTION

Technical Problem

An object of the present invention is to stably provide a thin-walled flexible medical tube having excellent kink resistance and tensile strength by a simple manufacturing method.

Solution to Problem

As a result of intensive studies in order to solve the problems, the inventors of the present invention provide (1) a method for manufacturing a medical tube, the medical tube including a coil layer on an inside of an outer layer tube made of a resin, the method including inserting the coil layer into the outer layer tube, and heating the outer layer tube at a molding temperature lower than a melting point of the outer layer tube, thereby bringing the outer layer tube into contact with the coil layer to slidably fix the outer layer tube onto the coil layer; and (2) a method for manufacturing a medical tube, the medical tube including an intermediate layer on an inside of an outer layer tube made of a resin and further including a coil layer on an inside of the intermediate layer, the method including disposing the intermediate layer and the coil layer in the outer layer tube, and heating the outer layer tube at a molding temperature lower than a melting point of the outer layer tube, thereby slidably fixing the outer layer tube onto the coil layer through the intermediate layer. These methods enable the stable supply of a thin-walled flexible medical tube having excellent kink resistance and tensile strength by the simple manufacturing method.

The inventors also provide (3) the manufacturing method in which the outer layer tube has an inner diameter shrinkage ratio of 10% or less during the heating at the molding temperature. The method enables the production of a medical tube at low cost and also enables the supply of a thinner-walled flexible medical tube regardless of a material of the outer layer tube as long as the outer layer tube has such a property by the simple manufacturing method.

The inventors also provide (4) the method for manufacturing a medical tube, in which an external force is applied to reduce the inner diameter of the outer layer tube during the heating at the molding temperature;

(5) the method for manufacturing a medical tube, in which the external force is applied by disposing a heat shrinkable tube on an outside of the outer layer tube and the heat shrinkable tube has an inner diameter capable of being shrunk;

(6) the method for manufacturing a medical tube, in which the external force is applied by a mold from an outside of the outer layer tube;

(7) the method for manufacturing a medical tube, in which the external force is applied by pulling the outer layer tube out of a die; and (8) the method for manufacturing a medical tube, in which the external force is applied by elongating the outer layer tube. These methods enable the stable supply of a medical tube having a further improved kink resistance.

The inventors also provide (9) the method for manufacturing a medical tube, in which the coil layer includes a metal wire; and

(10) the method for manufacturing a medical tube, in which the coil layer includes a wire having a flat shape. These methods enable the supply of a thinner-walled medical tube having an improved kink resistance.

The inventors also provide (11) the method for manufacturing a medical tube, in which the coil layer is a tightly wound coil. The method enables the supply of a medical tube having an improved flexural rigidity and an improved pushing-in strength in a longitudinal direction.

The inventors also provide (12) the method for manufacturing a medical tube, in which the coil layer is a pitch wound coil. The method enables the supply of a more flexible medical tube having an improved kink resistance.

The inventors also provide (13) the method for manufacturing a medical tube, in which the intermediate layer includes a material having a higher flexibility than that of a material of the outer layer tube;

(14) the method for manufacturing a medical tube, in which the intermediate layer includes a material having a melting point lower than that of the outer layer tube;

(15) the method for manufacturing a medical tube, in which the molding temperature is higher than a melting point of a material constituting the intermediate layer;

(16) the method for manufacturing a medical tube, in which the outer layer tube and the intermediate layer are a two-layer tube before applying the outer layer tube and the intermediate layer onto the coil layer; and

(17) the method for manufacturing a medical tube, in which the material of the intermediate layer is the same type as the material of the outer layer tube. These methods can prevent the coil from being displaced and enable the stable supply of a medical tube.

The inventors also provide (18) the method for manufacturing a medical tube, in which a second outer layer is provided on the outside of the outer layer tube and the second outer layer includes a material having a melting point lower than that of the outer layer tube. A medical tube obtained by the method can be easily joined to another tube or the like and can be applied to medical assemblies and catheters having various shapes.

The inventors also provide (19) the method for manufacturing a medical tube, in which the outer layer tube includes a thermoplastic elastomer. The method enables the supply of a more flexible medical tube having a high toughness and a more excellent kink resistance.

The inventors also provide (20) a medical tube manufactured by any of the manufacturing methods; and

(21) a medical device including the medical tube as at least one part. These inventions enable the supply of a thin-walled flexible medical tube having kink resistance and tensile strength and of a medical device using the medical tube by the simple manufacturing method.

Advantageous Effects of Invention

As described above, the present invention enables the stable supply of a thin-walled flexible medical tube having excellent kink resistance and tensile strength by the simple manufacturing method. As a result, the obtained medical tube can be effectively used as a component of a medical device such as various catheters.

DESCRIPTION OF EMBODIMENTS

A method for manufacturing a medical tube of the present invention and a medical tube manufactured by the manufacturing method will now be described.

The present invention relates to a method for manufacturing a medical tube. The method for manufacturing a medical tube is characterized by including inserting a coil layer into an outer layer tube made of a resin and heating the outer layer tube at a molding temperature lower than a melting point of the outer layer tube, thereby bringing the outer layer tube into contact with the coil layer to slidably fix the outer layer tube onto the coil layer. The manufacturing method is regarded as a first manufacturing method.

Such a manufacturing method enables the easy supply of a thin-walled flexible medical tube having excellent kink resistance and tensile strength without using a special structure or a manufacturing method for tensile strength reinforcement.

In the present invention, the "bringing the outer layer tube into contact with the coil layer to slidably fix the outer layer tube onto the coil layer" means that the outer layer tube and the coil layer are in contact with and fixed to each other, for example, by frictional force so as not to slide in a condition without applying any stress such as elongation and bending to a medical tube but, when such stress is applied, the outer layer tube and the coil layer can slide independently of each other before the outer layer tube cracks or is broken, more preferably, before the outer layer tube undergoes plastic deformation.

In the first manufacturing method of a medical tube of the present invention, the coil layer is inserted into the outer layer tube made of a resin and the outer layer tube is heated at a molding temperature lower than a melting point of the outer layer tube (in the present invention, a melting point of a resin constituting the outer layer tube may also be conveniently referred to as a melting point of the outer layer tube. The same shall be applied for the heat deformation temperature described later). As a result, regardless of a wound shape of the inside coil layer and a shape of the coil wire, the outer layer tube can be molded while substantially maintaining a uniform thickness of the original tube and thus the outer layer tube can ensure tensile strength and tensile elongation as a single-layer resin tube.

Figure 1:
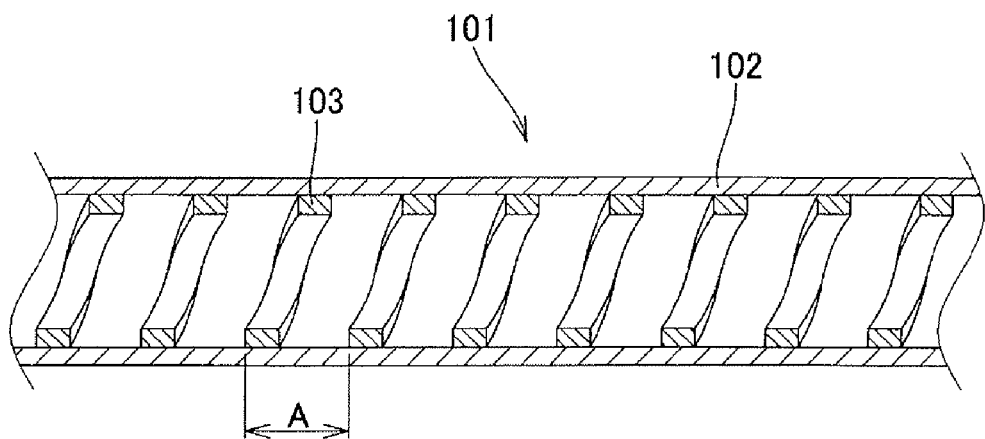
FIG. 1 is a schematic cross-sectional view of a medical tube in an axial direction as an example of an embodiment of a medical tube of the present invention.

The structure of a medical tube obtained by the method for manufacturing a medical tube of the present invention will be briefly described with reference to drawings while comparing with the structure of a medical tube obtained by a manufacturing method different from the method of the present invention. FIG. 1 shows an example of an embodiment of a medical tube obtained by the method for manufacturing a medical tube of the present invention. The embodiment exemplifies a case using a pitch wound coil described later as the coil layer. In the embodiment, a medical tube 101 includes a coil layer 103 including a pitch wound coil on the inside of a single-layer outer layer tube 102, and the outer layer tube 102 and the coil layer 103 are in contact with and slidably fixed to each other. The outer layer tube 102 has a substantially uniform thickness and has a substantially constant inner diameter without variation.

Figure 2:
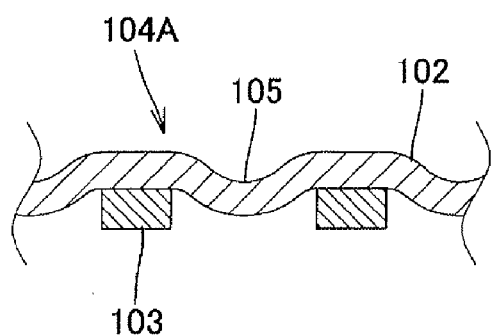
FIG. 2 is a partially enlarged cross-sectional view of a medical tube in an axial direction in another example of an embodiment of the medical tube of the present invention.

FIG. 2 shows a partially enlarged cross-sectional view of a medical tube in the axial direction as another example of an embodiment, obtained by the manufacturing method of the present invention. In the embodiment, unlike the example shown in FIG. 1, though concave parts 105 are formed, the outer layer tube 102 has a substantially uniform thickness regardless of the presence or absence of the coil layer disposed on the inside. In particular, even at a part 104A that is in contact with a coil wire edge at the inside of the outer layer tube 102, the outer layer tube 102 maintains the thickness. This is because the tube is molded at a temperature lower than the melting point. In such a condition, the resin basically does not flow in the axial direction, and this makes the thickness of the outer layer tube substantially constant in any cross section perpendicular to the axial direction regardless of the presence or absence of the coil wire.

Figure 3:
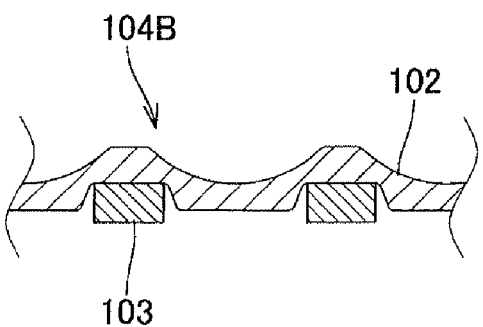
FIG. 3 is a partially enlarged cross-sectional view of a medical tube in an axial direction obtained by a manufacturing method different from the method for manufacturing a medical tube of the present invention.

FIG. 3 is a partially enlarged cross-sectional view of a medical tube in the axial direction obtained by a manufacturing method different from the method for manufacturing a medical tube of the present invention, namely, a medical tube obtained by heating the outer layer tube at a molding temperature higher than a melting point of the outer layer tube. When the outer layer tube is heated at a molding temperature higher than a melting point of the outer layer tube in this manner, depending on a wound shape of the coil layer or a shape of the coil wire, the wall thickness of the outer layer tube may vary at the edge of a coil wire, and this raises a problem in which the tensile strength and the tensile elongation are locally reduced. As shown in FIG. 3, the thickness of the outer layer tube 102 is locally reduced. In particular, at a part 104B that is in contact with a coil wire edge at the inside of the outer layer tube 102, the thickness of the outer layer tube 102 is reduced. This is because the tube is molded at a temperature higher than the melting point. In such a condition, the resin is melted and a resin at the coil wire edge is likely to flow to a part that is not in contact with the coil wire, and this locally reduces the thickness of the outer layer tube 102 at the part 104B that is in contact with the coil wire edge at the inside of the outer layer tube 102. The phenomenon is particularly readily caused when the wound shape of the coil layer or the shape of the coil wire is a pitch wound coil or a flat shape described later, respectively, or when a force is applied to the outer layer tube from the outside as described later. Thus, when an outer layer tube is heated at a molding temperature higher than a melting point of the outer layer tube, the outer layer tube is required to have a very large wall thickness in order to ensure the tensile strength or the tensile elongation. However, a tube having an increased outer diameter in order to increase the wall thickness is highly invasive and cannot be used for peripheral treatment of a thinner lumen in the body, while a tube having a reduced inner diameter raises problems in which the injection performance of a medicinal agent, the aspiration performance of a blood clot, and the delivery performance of other catheters are remarkably impaired. A thick-walled outer layer tube is kinked by a large force, and such a tube is kinked together with the coil layer, thereby raising a problem in which surgery is not continuously carried out.

In this manner, when a tube is heated for the molding at a molding temperature at which a member containing a polymer layer is fused, for example, as described in Patent Document 1, it has been difficult to manufacture a thin-walled flexible medical tube having excellent kink resistance and tensile strength as intended by the present invention.

In the present invention, the molding temperature may be any temperature as long as the temperature is lower than a melting point of a resin constituting the outer layer tube. However, the molding temperature is preferably lower than the melting point and also higher than a heat deformation temperature (deflection temperature under load) of the resin. A molding temperature higher than the heat deformation temperature (deflection temperature under load) can achieve tighter contact (closer contact) of the outer layer tube with the coil layer. For example, when an outer layer tube having an inner diameter shrinkage ratio of 10% or less during the heating at a predetermined molding temperature is used, such an outer layer tube can be more uniformly shrunk to be brought into tighter contact (closer contact) with the coil layer. When an external force is applied to reduce the inner diameter of the outer layer tube as described later, the molding temperature is preferably higher than a heat deformation temperature (deflection temperature under load) of the outer layer tube because such a temperature enables the outer layer tube to be more uniformly shrunk in the diameter direction. Such uniform shrinkage of the outer layer tube enables the outer surface of a coil constituting the coil layer to come in closer contact with the inner surface of the outer layer tube, and this can further improve the kink resistance.

In the method for manufacturing a medical tube of the present invention, the outer layer tube is brought into contact with the coil layer to be slidably fixed onto the coil layer by the predetermined operation above.

The contact and slidably fixed state between the outer layer tube and the coil layer is formed as above. Hence, when a medical tube obtained by the manufacturing method of the present invention is pulled to be elongated, the coil and the outer layer tube can move independently because they are not secured. Therefore, the outer layer tube can ensure tensile strength and tensile elongation as a single-layer resin tube. In addition, when the medical tube is highly bent, the coil layer and the outer layer tube move independently. Therefore, the medical tube can ensure fine kink resistance.

Here, the securing means that the outer layer tube and the coil layer are fixed to each other while the outer layer tube and the coil layer do not slide and do not move independently before the outer layer tube cracks or is broken or before the outer layer tube undergoes plastic deformation when stress such as tensile stress is applied to a medical tube formed.

For example, when the outer surface of a coil and the inner surface of an outer layer tube are secured by a method of heating at a molding temperature higher than a melting point of the outer layer tube as described in Patent Document 1 or by a common method of using an adhesive between the coil layer and the outer layer tube, the outer layer tube part secured to the coil outer surface is pulled together with the coil at the time that such a medical tube is pulled and elongated. Then, the outer layer tube between wires of the coil alone is locally elongated, and therefore, the tensile strength and the tensile elongation are remarkably reduced. During the operation of a catheter in a clinical practice, also in order to safely remove the catheter that, for example, is caught in the body, a medical tube used for a catheter is required a certain degree of tensile strength and tensile elongation. A tube having a low tensile strength may be readily broken, while a tube having a high tensile strength but having a low tensile elongation may not endure sudden removal. By the method using an adhesive between the coil and the outer layer tube, a medical tube to be obtained has a limited structure. For example, an inner layer is required to be included or the coil wound shape is required to be a tightly wound shape described later in order to prevent the adhesive from spilling into an inner cavity of the medical tube.

In contrast, in a medical tube obtained by the manufacturing method of the present invention, the outer surface of the coil and the inner surface of the outer layer tube are in contact with and slidably fixed to each other. Thus, when the medical tube is pulled and elongated, the coil and the outer layer tube independently move and the whole outer layer tube can receive the tensile stress. This prevents the outer layer tube from being locally elongated at a particular position, resulting in a thin-walled flexible medical tube having excellent kink resistance and tensile strength. In addition, the method does not need the use of an adhesive. This eliminates the arrangement of an inner layer in order to prevent the adhesive from spilling into an inner cavity of the medical tube and the limitation of a coil constituting the coil layer to a tightly wound coil. Therefore, such a structure enables a medical tube to ensure a large inner diameter and enables the coil layer structure to be appropriately selected depending on, for example, an application of the medical tube.

Although the method of the present invention needs no adhesive as described above, the outer layer tube may be fixed to the coil layer with an adhesive or the like within a range not causing breakage of the medical tube or not causing plastic deformation of the outer layer tube. When, for example, a medical tube obtained by the manufacturing method of the present invention is used to prepare a medical device as described later, an end of the medical tube may be fixed with an adhesive or the like, and also, the outer layer tube and the coil layer may be fixed at an end.

In the present invention, depending on an application of the medical tube, an inner layer may be provided on the inside of the coil layer as long as the inner diameter can be ensured.

The medical tube could have a structure in which a coil is simply disposed in the outer layer tube and the outer surface of the coil is in little contact with the inner surface of the outer layer tube. However, when a tube having such a structure is highly bent, the coil is freely bent, and this causes, for example, displacement, folding, or overlapping of the coil. In such a condition, the inner and outer diameters of the tube may be changed or the tube may be kinked, making almost impossible the continuation of surgery.

The configurations such as a wire shape, a wire size, and a wound shape of the coil layer used in the method for manufacturing a medical tube of the present invention are not particularly limited. The wire shape may be a common round wire or a flat wire described later, for example. The wound shape may be a tightly wound shape described later or a pitch wound shape, for example. Further, each configuration may be different depending on a part of a medical tube.

The configuration of the coil layer may be suitably selected depending on an application of the medical tube. For example, when a tube needs kink resistance and tensile strength of a shaft as well as a certain degree of flexural rigidity and pushing-in strength in the longitudinal direction as a hand shaft of a catheter, the wire shape is preferably a flat wire shape and the wound shape is preferably a tightly wound shape. However, the coil layer may have at least one configuration of the flat wire shape and the tightly wound shape. In addition, in order to reduce the wall thickness of the medical tube or to ensure a larger inner diameter of the medical tube, the wire shape is preferably a flat wire shape.

When a coil layer used is composed of a tightly wound flat wire as the wire as above, a medical tube obtained by the manufacturing method of the present invention has a thin wall but obtains high flexural rigidity and high pushing-in strength in the longitudinal direction.

The flat wire does not have a round-shaped cross section but has a shape with a thickness and a width and is typically obtained by rolling a so-called round wire that is a wire having a round-shaped cross section. The flat wire in the present invention also includes a so-called flat wire that is a wire having upper and lower faces substantially parallel and having both ends rounded and a so-called rectangular wire that is a wire having a substantially rectangular cross section.

The tightly wound shape is a wound shape in which a wire is wound so that adjacent wires are at least close to or in contact with each other.

The tightly wound coil used may be a coil having a compressive force (force generally called initial tension) between wires adjacent to each other in a coil longitudinal direction. In this manner, a coil that has an initial tension as high as possible and in which adjacent wires are not displaced further enables a shaft to have improved flexural rigidity and pushing-in strength.

In this manner, as the configuration of a coil layer used in the method for manufacturing a medical tube of the present invention, when a medical tube obtained by the manufacturing method is used, for example, as a hand shaft of a catheter, the coil layer preferably has a configuration in which the wire has a flat wire shape and/or the wound shape is a tightly wound shape. The tightly wound coil preferably has initial tension. In addition, the coil layer more preferably has a configuration in which the wire has a flat wire shape and the wound shape is a tightly wound shape having initial tension. A medical tube obtained by using the coil layer having such a configuration is especially suitable for a hand shaft of a catheter that may be much highly bent during surgery in a clinical practice.

For example, as a shaft at the leading end of a catheter, when flexibility of a shaft is required in addition to the kink resistance and tensile strength of a shaft, the wound shape is preferably a pitch wound shape. The pitch wound shape is a wound shape in which a wire is wound so as to give a clearance between wires adjacent to each other. In particular, in the length in the longitudinal direction of a medical tube, the clearance between a coil wire and the adjacent wire is preferably the same as or longer than the width of the coil wire. Such a structure can achieve a more flexible shaft having excellent kink resistance. Here, the pitch means a length in the longitudinal direction between a certain point on a wire of the coil and another point one circumference (360 degree) apart in the circumferential direction along the wire (exemplified by A in FIG. 1). In more detail, the pitch is the sum of the width of a wire in the longitudinal direction and the clearance between the wires. Therefore, "the clearance between a coil wire and the adjacent wire being the same as or longer than the width of the coil wire" in the present invention means that the pitch is 2t or longer where the width of the wire is t.

When a pitch wound coil layer is used as above, a method of heating the outer layer tube at a molding temperature higher than the melting point of the outer layer tube, for example, as described in Patent Document 1, leads to variation in the wall thickness of the outer layer tube as described above and particularly readily raises a problem in which the tensile strength and the tensile elongation are significantly reduced. To address the problem, when the wall thickness of an outer layer tube is increased in order to ensure the tensile strength, the outer diameter of the tube is increased and the tube loses the flexibility. This significantly reduces insert performance of the tube. Hence, such a tube is difficult to be used as the shaft at the leading end of a catheter that is inserted into a most peripheral lumen in the body.

In the method for manufacturing a medical tube of the present invention, the outer layer tube is heated at a molding temperature lower than a melting point of the outer layer tube. Thus, the method does not cause the variation in the wall thickness of the outer layer tube as described above. In addition, the outer surface of a wire constituting the coil layer and the inner surface of the outer layer tube are in contact with and slidably fixed to each other. As a result, the outer layer tube is not locally elongated at a particular position, and the tensile strength and the tensile elongation can be ensured. This enables the medical tube to maintain flexibility and to have kink resistance. Such a medical tube can be smoothly inserted without kink even when the medical tube is inserted into a highly bent peripheral lumen in the body. Such a medical tube can also maintain its inner cavity even when the medical tube is highly bent, thereby maintaining the injection performance of a medicinal agent, the aspiration performance of a blood clot, and the delivery performance of another catheter. A pitch wound coil layer is particularly preferably used as a shaft at the leading end of a catheter because the medical tube obtained by the manufacturing method of the present invention has the characteristics as above.

Examples of the material of the wire constituting the coil layer used in the present invention include various materials such as a metal and a resin. Particularly preferred materials are stainless steel and a material having high radiopacity, for example, a metal such as tungsten, platinum, iridium, and gold. Among them, particularly preferred are spring stainless steel, tungsten, and the like having high elastic modulus in tension of a wire. By using such a wire, a medical tube having a thinner wall thickness and improved kink resistance can be manufactured.

The resin constituting the outer layer tube used in the present invention is not particularly limited.

For example, when a medical tube manufactured by using an outer layer tube is integrated in a medical device such as a catheter and is joined to another member, the resin may be appropriately selected considering the joining method such as welding and adhesion and depending on a member constituting the medical device.

Examples of the resin usable for the outer layer tube include, but are not limited to, polyamides such as nylon 6, nylon 66, nylon 12, and a polyamide elastomer; olefins such as polyethylene, polypropylene, polymethyl methacrylate, and modified polyolefin; polyesters such as polyethylene terephthalate, polybutylene terephthalate, and a polyester elastomer; polyurethane; a polyurethane elastomer; polyether ether ketone; polymer blends of them, and polymer alloys of them.

Among these resins, from the viewpoint of easy preparation of the outer layer tube, a resin usable for extrusion molding is preferred; from the viewpoint of easy joining to other various tubes, a thermoplastic elastomer is preferred; and from the viewpoint of increasing toughness when a tube is highly bent, a polyamide elastomer and a polyurethane elastomer are more preferred.

The resin may further include, in addition to a polymerization auxiliary used during polymerization, various additives such as a contrast medium, a plasticizer, a reinforcement, and a pigment.

The outer layer tube can be molded by a known method such as injection molding and extrusion molding. A long outer layer tube is preferably molded by extrusion molding. When the inner diameter of an outer layer tube is reduced during heating at a predetermined molding temperature, from the viewpoint of well shrinkage of the outer layer tube by residual stress, the outer layer tube is preferably molded through extrusion molding by common pulling down while injecting air into an inner cavity. The extrusion molding has an advantage in easy production and production cost because the method is a common method not employing a special process (such as an electron beam irradiation process and core material coating).

In addition, the extrusion molding enables the production of a thin-walled tube maintaining the flexibility of an original material, and therefore a flexible medical tube having a very thin wall thickness can be manufactured.

In the method for manufacturing a medical tube of the present invention, a second outer layer can be formed on the outside of the outer layer tube. In this case, the melting point of a material used constituting the second outer layer (hereinafter, simply referred to as melting point of the second outer layer) is preferably lower than a melting point of the outer layer tube. By heating the second outer layer at a temperature higher than a melting point of the second outer layer and lower than a melting point of the outer layer tube, the second outer layer alone can be melted and an additional tube can be joined to the outer surface of the medical tube by, for example, welding. This enables the medical tube of the present invention to be easily applied to medical assemblies and catheters having various shapes. Examples of the material constituting such a second outer layer include resins that constitute the outer layer tube. However, it is significant to select a resin having characteristics different from those of a resin constituting the outer layer tube depending on a purpose.

The second outer layer is formed on the outside of the outer layer tube by any manufacturing method. From the viewpoint of easy manufacturing, the second outer layer is preferably formed on the outside of the outer layer tube to form a two-layer tube shape before the outer layer tube and the coil layer are in contact with and slidably fixed to each other. Such a two-layer tube can be prepared by, for example, multilayer extrusion molding (co-extrusion molding) or dip molding. When the inner diameter of the two-layer tube (that is also the inner diameter of the outer layer tube) is reduced during the heating at a predetermined molding temperature, the tube is preferably prepared through multilayer extrusion molding by common pulling down while injecting air into an inner cavity.

When the second outer layer is formed on the outside of the outer layer tube, in order not to increase the outer diameter of the medical tube as much as possible, the sum of the wall thickness of the outer layer tube and the wall thickness of the second outer layer is preferably substantially the same as the wall thickness without the second outer layer.

The second outer layer may be provided along the full length of the medical tube or may be partially provided.

Examples of the method of heating the outer layer tube at a predetermined molding temperature, thereby bringing the outer layer tube into contact with the coil layer to slidably fix the outer layer tube onto the coil layer, include, but are not necessarily limited to, a method of applying the outer layer tube onto the coil layer. Examples of the applying the outer layer tube onto the coil layer as above include a method of reducing the inner diameter of the outer layer tube into which the coil layer is inserted, by 10% or less during the heating at a predetermined molding temperature. Examples of the method of causing such a reduction include, but are not necessarily limited to, a method of using residual stress when the outer layer tube itself is molded and a method of applying an external force to reduce the inner diameter of the outer layer tube.

The reduction ratio in the "reducing the inner diameter of the outer layer tube by 10% or less" means the reduction ratio comparing an inner diameter of the outer layer tube before the coil layer is inserted to an inner diameter of the outer layer tube at a part in contact with the coil layer after the heating at a predetermined temperature, thereby bringing the outer layer tube into contact with the coil layer to slidably fix the outer layer tube onto the coil layer.

The method of using residual stress can be exemplified by the following method. The coil layer is inserted into the outer layer tube. The outer layer tube is heated at a molding temperature lower than a melting point of the outer layer tube, thereby using the residual stress generated when, for example, the outer layer tube itself is molded. As a result, the inner diameter of the outer layer tube can be reduced.

In the technical field, a process of removing the residual stress generated at the time of molding of a typical tube as much as possible is commonly carried out after the molding because the residual stress causes dimensional change or shape change of the tube due to, for example, the subsequent assembly, sterilization, and heat treatment of a medical device. In contrast, in the present invention, such a residual stress is positively used in the method of manufacturing a medical tube. This enables the use of an outer layer tube having an inner diameter larger than that of the coil layer. Therefore, the coil layer can be easily disposed in the outer layer tube, and the outer layer tube and the coil can be in contact with and slidably fixed to each other. In addition, even when the residual stress remains at the time of molding into an intended shape, the heating at a predetermined molding temperature can relax the stress.

Even when the residual stress is used in this manner, the outer layer tube can be prepared through extrusion molding by common pulling down without using any special process. Hence, the outer layer tube can be prepared at low cost. The multilayer extrusion molding by pulling down makes the use of a two-layer tube having the second outer layer in place of a single-layer outer layer tube very easy.

With regard to the shrinkage ratio of an outer layer tube by the residual stress, the outer layer tube preferably has an inner diameter shrinkage ratio of 1% or more and 10% or less during the heating at a molding temperature. The outer layer tube having such a shrinkage ratio can be prepared by a common extrusion molding and causes a small change in the wall thickness after the shrinkage. Therefore, a thin-walled medical tube can be manufactured. An outer layer tube having a shrinkage ratio of less than 1% is likely to cause the displacement of a coil when the coil is inserted into the outer layer tube, and hence the stable supply of an intended medical tube is likely to be difficult.

In the present invention, during the heating at a molding temperature lower than a melting point of the outer layer tube as described above, an external force may be applied to reduce the inner diameter of the outer layer tube. By applying such an external force, the outer layer tube comes in tighter contact with the coil. This enables the outer layer tube to be in closer contact with the coil layer, thereby further improving the kink resistance of a medical tube to be obtained. An outer layer tube even having a low roundness can be forcibly in contact with the coil over the entire circumference in the diameter direction by the external force. Therefore, a medical tube having stable kink resistance can be manufactured. In addition, any outer layer tube can be used regardless of the molding method of the outer layer tube used.

Examples of the method of applying such an external force include a method of applying a heat shrinkable tube from the outside of the outer layer tube, a method of applying an external force by a mold from the outside of the outer layer tube, a method of elongating the outer layer tube, and a method of pulling the outer layer tube out from a die.

Among these methods, the method of applying a heat shrinkable tube, the method of applying an external force by a mold, and the method of pulling the outer layer tube out from a die are more preferred. These methods are preferably carried out while heating a heat shrinkable tube, a mold, or a die so that the molding temperature reaches lower than a melting point of the outer layer tube.

By these methods, a high external force can be stably applied from the entire circumference in the diameter direction of the outer layer tube. This enables the outer layer tube to come in tighter contact with the coil, thereby further improving the kink resistance.

In addition, by the shrinkage of the heat shrinkable tube along the shape of an inner tube, or by designing the inner shape of a mold or a die, a medical tube having any shape can be manufactured. Needless to say, these molding methods may be used in combination. For example, after shrinking the inner diameter by the residual stress of the outer layer tube itself, an additional external force may be further applied by a heat shrinkable tube or a mold, or after elongating the outer layer tube thereby to shrink the inner diameter, an additional external force may be further applied by a heat shrinkable tube or a mold.

Among them, with regard to the method using a heat shrinkable tube, a typical method for forming a resin layer on a coil in the conventional technical field is that a tube to be the resin layer is further covered with a heat shrinkable tube and the tube is heated at a temperature higher than a melting point of the tube in the heat shrinkable tube thereby to be melted.

In contrast, the present invention employs a method of applying a heat shrinkable tube onto the outside of the outer layer tube and heating the tube at a molding temperature lower than a melting point of the outer layer tube. By adopting such a method, the outer layer tube and the coil can be in contact with and slidably fixed to each other. A tube manufactured by the conventional method at a high temperature as above cannot provide such excellent performance as a medical tube obtained by the method for manufacturing a medical tube of the present invention as described above. In addition, such a conventional method needs to select the resin layer of the tube and the heat shrinkable tube from different materials to each other. This is because, when the resin layer and the heat shrinkable tube, which is required to be removed after molding, are made of the same material, the resin layer is melted to be secured to the heat shrinkable tube and this may interfere with the removal of the heat shrinkable tube. Thus, such a conventional method has a case in which there is no suitable heat shrinkable tube depending on a material of the resin layer or has a case in which a polytetrafluoroethylene heat shrinkable tube or the like having a very high heat shrinkage temperature is required to be used, thereby extremely deteriorating workability. In contrast, in the present invention, the outer layer tube is heated at a molding temperature lower than or equal to a melting point of the outer layer tube. Thus, a most appropriate material can be selected to be used for the heat shrinkable tube depending on the type of a resin constituting the outer layer tube as long as the material is shrunk at a predetermined molding temperature. Therefore, a medical tube can be reliably molded. The heat shrinkage temperature of the heat shrinkable tube is not particularly limited as long as the heat shrinkable tube can be shrunk at a predetermined molding temperature. The heat shrinkage temperature may be equal to or lower than a molding temperature and is preferably lower than a molding temperature. This enables the outer layer tube or the intermediate layer to surely come in tighter contact with the coil, thereby further improving the kink resistance. The shrinkage ratio of the heat shrinkable tube is also not particularly limited, and a heat shrinkable tube having such a shrinkage ratio as to enable the molding of a medical tube to obtain an intended outer diameter and shape at a predetermined molding temperature may be appropriately selected.

When an external force is applied by a mold from the outside of the outer layer tube, as with the case of the method by a heat shrinkable tube, in the conventional technical field, a resin is typically melted at a temperature higher than a melting point of the resin to be molded.

However, in the present invention, a mold is disposed on the outside of the outer layer tube and the outer layer tube is heated at a molding temperature lower than a melting point of the outer layer tube. This enables the outer layer tube and the coil to be in contact with and slidably fixed to each other. In this case, the mold preferably has a configuration capable of heating the outer layer tube at a molding temperature lower than a melting point of the outer layer tube. The configuration enables the application of an external force by the mold while heating the outer layer tube at a molding temperature and enables the outer layer tube to come in tighter contact with the coil. The cross sectional shape of the mold can be fit to a medical tube to be molded and may be any shape, for example, a perfect circle shape, an ellipse shape, and a figure-eight shape. When the cross sectional shape of a medical tube to be manufactured is substantially a perfect circle, the mold is preferably equipped with a mechanism in which the inner diameter is gradually reduced. A mold equipped with such a mechanism enables the coil and the outer layer tube to be in tighter contact with each other. Examples of the mechanism of such a mold include, but are not limited to, a mold having two plates. The mold is configured so that an outer layer tube having a coil layer in the tube is disposed between a movable plate and a fixed plate that are designed so as to form a space corresponding to an intended tube shape, then the movable plate is operated to reduce the distance between the movable plate and the fixed plate, and the tube finally obtains the intended shape in the space.

Also in the case of applying an external force by pulling the tube out from a die, the die preferably has a configuration capable of heating the outer layer tube at a molding temperature lower than a melting point of the outer layer tube. The configuration enables the application of an external force by pulling the tube out from the die while heating the outer layer tube at a molding temperature and enables the outer layer tube to come in tighter contact with the coil.

Examples of such a die include a die having openings at both ends and including a continuous hollow portion having a diameter that is continuously or stepwisely reduced from one opening toward the other opening. The shape of one opening or a part near one opening of the die is designed so as to include a part having an inner diameter that corresponds to the outer diameter of an intended medical tube. The shape of the other opening is not particularly limited and may be a shape through which an outer layer tube before molding can be passed. The overall structure of the die may be a structure either capable of being separated or incapable of being separated as long as the hollow portion shape corresponding to the shape of an intended medical tube can be formed.

The molding method using such a die will be briefly described. Into a hollow portion of a die set at a predetermined molding temperature, an outer layer tube having a coil layer in the tube is inserted from one opening of the die. Then, the outer layer tube and others are passed through the hollow portion and are pulled out from the other opening having an intended shape. As a result, a medical tube molded into an intended shape can be obtained.

The die and the molding method using the die above are merely examples, the present invention is not limited to them, and the die and the molding method may be appropriately modified.

The first manufacturing method in the present invention and the basic configuration of the medical tube obtained by the manufacturing method are principally as described above. Other items common between the first and second manufacturing methods and between the medical tubes obtained by these manufacturing methods will be described together after a basic configuration of the second manufacturing method of the present invention is described.

The present invention relates to a method for manufacturing a medical tube that includes an intermediate layer on an inside of an outer layer tube made of a resin and further includes a coil layer on an inside of the intermediate layer. The method for manufacturing a medical tube is characterized by including disposing the intermediate layer and the coil layer in the outer layer tube, and heating the outer layer tube at a molding temperature lower than a melting point of the outer layer tube, thereby slidably fixing the outer layer tube onto the coil layer through the intermediate layer. The manufacturing method is regarded as a second manufacturing method.

Such a manufacturing method enables the easy supply of a thin-walled flexible medical tube having excellent kink resistance and tensile strength without using a special structure or a manufacturing method. In the medical tube obtained by the manufacturing method (second manufacturing method) of the present invention, an outer layer tube is slidably fixed onto the coil layer through the intermediate layer. Hence, even when the medical tube is pulled and elongated, the coil layer and the outer layer tube independently move and the whole outer layer tube can receive the tensile stress. This prevents the outer layer tube from being locally elongated at a particular position, resulting in a thin-walled flexible medical tube having excellent kink resistance and tensile strength.

In the present invention, the "slidably fixing the outer layer tube onto the coil layer through the intermediate layer" means that the outer layer tube and the coil layer are in contact with and fixed to each other, for example, by frictional force so as not to slide in a condition without applying any stress such as elongation and bending to a medical tube but, when such stress is applied, the coil layer and the outer layer tube can slide independently of each other through the intermediate layer before the outer layer tube cracks or is broken, more preferably, before the outer layer tube undergoes plastic deformation. The term "through the intermediate layer" means that, when the intermediate layer slides together with the coil layer, the intermediate layer may slide together with the outer layer tube. The "fixing" is a concept that includes the condition in which the intermediate layer is separably joined to the coil layer or to the outer layer tube before the outer layer tube cracks or is broken, more preferably, before the outer layer tube undergoes plastic deformation.

The configurations of the coil layer and the outer layer tube and the molding temperature used in the second manufacturing method will not be described in detail in the manufacturing method because they may be the same as the configurations and the molding temperature in the first manufacturing method, and hence basic characteristics of the manufacturing method will be described below.

Preferably, the intermediate layer is uniformly disposed on a medical tube in the longitudinal direction. The intermediate layer may be configured as a tube including the intermediate layer alone before the intermediate layer is disposed on the coil layer or may be configured as a two-layer tube including the intermediate layer as the inner layer and the outer layer tube as the outer layer. Such a structure enables the intermediate layer to be easily disposed between the coil layer and the outer layer tube. Among them, the two-layer tube is preferably used in order to easily manufacture a medical tube. In particular, it is difficult for a person skilled in the art to prepare a tube including the intermediate layer alone having a very small wall thickness (for example, a wall thickness of about 10 μm or less) in the present technology. When the two-layer tube including the intermediate layer as the inner layer and the outer layer tube as the outer layer is formed before the intermediate layer is applied onto the coil layer, an intermediate layer having such a small wall thickness that cannot be achieved by a tube including the intermediate layer alone can be prepared.

Such a two-layer tube can be prepared by, for example, multilayer extrusion molding (co-extrusion molding) or dip molding. Among them, for example, in the same manner as described in the first manufacturing method, the two-layer tube is preferably molded through multilayer extrusion molding by pulling down when the two-layer tube is used in place of the single-layer outer layer tube and the residual stress is used, thereby slidably fixing the outer layer tube onto the coil layer through the intermediate layer.

Also in the second method for manufacturing a medical tube of the present invention, the outer layer tube is heated at a molding temperature lower than a melting point of the outer layer tube. Thus, regardless of a shape of the coil layer in the outer layer tube, at least the outer layer tube can be molded while substantially maintaining a uniform thickness of the original tube. Therefore, the outer layer tube can ensure tensile strength and tensile elongation as a single-layer resin tube.

Also in the second manufacturing method as above, the molding temperature is only required to be lower than a melting point of the outer layer tube. However, as described in the first manufacturing method, the molding temperature is preferably higher than a heat deformation temperature (deflection temperature under load) of the outer layer tube.

Though the second manufacturing method also adopts the molding temperature as above, the intermediate layer is disposed in the outer layer tube in the manufacturing method. Hence, by considering the melting point and the heat deformation temperature of a material constituting the intermediate layer, the medical tube obtained by the second manufacturing method can obtain further improved function.

The material constituting the intermediate layer is not particularly limited and, for example, a resin constituting the outer layer tube can be used. When such a resin is used, from the relation with the molding temperature in the present invention, preferably used is a resin having a melting point equal to or lower than a melting point of a resin constituting the outer layer tube, and more preferably used is a resin having a melting point lower than a melting point of a resin constituting the outer layer tube.

When the molding temperature is lower than melting points of the outer layer tube and the intermediate layer, the intermediate layer behaves in a manner similar to the outer layer tube. Therefore, a medical tube having, for example, a cross sectional structure as shown in FIG. 1 or FIG. 2 can be manufactured. Needless to say, the outer layer tube 102 part in FIG. 1 and FIG. 2 has a two-layer structure. The molding temperature is more preferably higher than heat deformation temperatures of the outer layer tube and the intermediate layer.

Figure 4:
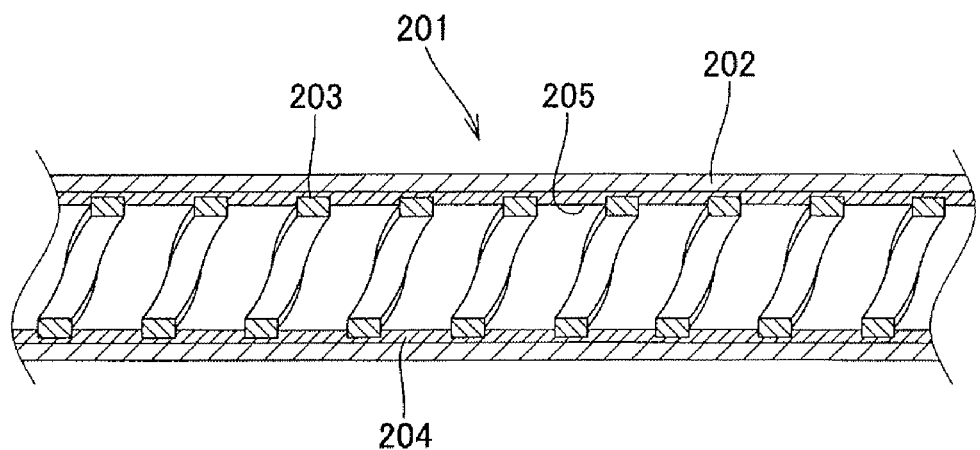
FIG. 4 is a schematic cross-sectional view of a medical tube in an axial direction as an example of another embodiment of the medical tube of the present invention.

In contrast, when the molding temperature is lower than a melting point of the outer layer tube and higher than a melting point of the intermediate layer, the intermediate layer alone is melted. Then, in the case that the intermediate layer alone is melted, depending on the machining condition, the coil shape of a wire constituting the coil layer, and the like, for example, when a pitch wound coil is used as the coil layer and the inner diameter of the outer layer tube is reduced, the intermediate layer enters between wires of the pitch wound coil, and this enables the pitch wound coil to be stably held. An example in this case is schematically shown in FIG. 4. As shown in FIG. 4, an outer layer tube 202 of a medical tube 201 has a substantially uniform wall thickness and an intermediate layer 204 and a coil layer 203 as a pitch wound coil are disposed on the inside of the outer layer tube 202. The intermediate layer 204 is disposed between wires 205 of the pitch wound coil. Depending on a machining condition or the like, the intermediate layer 204 remains or does not remain between an outer peripheral face of the wire of the pitch wound coil constituting the coil layer 203 and an inner peripheral face of the outer layer tube 202. FIG. 4 shows an example in which the intermediate layer 204 remains.

When the intermediate layer has a melting point lower than a molding temperature as above, the intermediate layer is generally likely to be joined (welded) to the coil layer and the outer layer tube. However, these components are joined but are not "secured" called in the present invention. Thus, for example, when the wound shape of a wire constituting the coil layer is a pitch wound shape, an intermediate layer that is melted and joined to the coil layer can suppress the displacement of the coil pitch, resulting in the stable supply of a medical tube. From such a viewpoint, the molding temperature is preferably higher than a melting point of the intermediate layer.

Unlike a commonly used adhesive, the joint degree of the intermediate layer to the outer layer tube and to the coil layer can be easily controlled as described above.

As other characteristics except the thermal characteristics of a material constituting the intermediate layer, the material constituting the intermediate layer preferably has higher flexibility than that of a resin constituting the outer layer tube. Such characteristics can more readily achieve a medical tube in which the outer layer tube ensures tensile strength while the intermediate layer is slidably fixed.

Exemplary combinations of resins of the outer layer tube and the intermediate layer will be described below.

For example, in the case that the materials of the outer layer tube and the intermediate layer are the same type, an intermediate layer having a melting point lower than the molding temperature and made of a material having higher flexibility than that of a material of the outer layer tube leads to low joint degree with the coil layer. Thus, the joint between the intermediate layer and the coil layer is broken when a medical tube is pulled and elongated. As a result, the coil and the outer layer tube can move independently. The phenomenon is more remarkable when the intermediate layer has a smaller wall thickness than that of the outer layer tube. Therefore, the intermediate layer is preferably as thin as possible.

In the case that the materials of the outer layer tube and the intermediate layer are different types to each other, the joint degree between the intermediate layer and the outer layer tube is generally low. Thus, the joint between the outer layer tube and the intermediate layer is broken when a medical tube is pulled and elongated. As a result, the coil layer and the outer layer tube can move independently. Even when the materials are different types, the joint degree between the intermediate layer and the coil layer may be low as with the case that the materials are the same type. Also from such a viewpoint, the intermediate layer preferably has a smaller wall thickness than that of the outer layer tube and is preferably made of a resin having high flexibility.

As for the strength of peeling between the intermediate layer and the coil layer or of peeling between the outer layer tube and the intermediate layer, the intermediate layer is preferably peeled before the outer layer tube cracks or is broken, more preferably, before the outer layer tube starts to undergo plastic deformation when stress is applied. Such a peel strength enables the coil and the outer layer tube to move independently. Therefore, the outer layer tube can ensure tensile strength and tensile elongation as a single-layer resin tube. The same types of materials as used herein means that materials are, for example, polyamide elastomers alone or polyurethane elastomers alone.

Also in the second manufacturing method, as with the first manufacturing method, the outer layer tube preferably has an inner diameter shrinkage ratio of 10% or less during the heating at a predetermined molding temperature. The reduction ratio means the reduction ratio comparing an inner diameter of the outer layer tube before the coil layer is inserted to an inner diameter of the outer layer tube at a part in close contact with the outside of the coil layer after heating the tube at a predetermined temperature, thereby bringing the outer layer tube in contact with the coil layer to slidably fix the outer layer tube onto the coil layer.

The method of heating the outer layer tube at a predetermined temperature, thereby slidably fixing the outer layer tube onto the coil layer through the intermediate layer is not particularly limited and the method described in the first manufacturing method may be employed. However, in the second manufacturing method, in place of the single-layer outer layer tube and the two-layer tube including the second outer layer on the outside of the single-layer outer layer tube in the first manufacturing method, a two-layer tube including the intermediate layer as the inner layer and the outer layer tube as the outer layer and a three-layer tube including the second outer layer on the outside of the two-layer tube may be used. When such a two-layer tube or a three-layer tube is used, in a manner similar to that in the first manufacturing method, by using residual stress of each tube or by applying an external force by, for example, a heat shrinkable tube, a mold, a die, or elongation of the two-layer tube or the three-layer tube, the inner diameter of the outer layer tube (namely, the two-layer tube or the three-layer tube) can be reduced.

Items common to the first and second manufacturing methods will be described below.

In the first manufacturing method of the present invention, the outer layer tube is brought into contact with and slidably fixed onto the coil layer, while in the second manufacturing method, the outer layer tube is slidably fixed onto the coil layer through the intermediate layer. Thus, in each manufacturing method, the outer layer tube and the coil layer or the intermediate layer and the coil layer are in contact with and fixed to each other. As the contact condition, the outer layer tube and the coil layer or the intermediate layer and the coil layer are preferably in contact with each other on about a half or more of the circumferential length in the cross section in the diameter direction of a medical tube. In a tube in contact in a half or less of the area, a half or more of the coil in the cross section in the diameter direction is freely bent when the tube is highly bent. Hence, such a tube is highly likely to cause, for example, displacement, folding, or overlapping of the coil. In such a condition, the inner and outer diameters of a shaft may be changed or a shaft may be kinked. This makes the continuation of surgery impossible. A tube in contact in a half or more of the area prevents the coil from being in such a condition and makes the continuation of surgery possible. The outer layer tube and the coil layer or the intermediate layer and the coil layer are preferably in slidable contact with each other substantially over the entire circumference in the cross section in the diameter direction. This can more highly prevent the coil layer from being displaced, bent, and overlapped and make the kink resistance stable and more improved.

The tensile elongation and the tensile strength in the present invention mean tensile breaking elongation and tensile breaking strength, and in the present invention, mean a maximum displacement and a maximum load when a part of the medical tube except the coil is broken. This is because the tensile elongation when a coil is broken is very large, the breaking elongation and the breaking strength of a coil are less important in a medical tube, and the breaking elongation and the breaking strength of a part except the coil is important in a medical tube.

The melting point in the present invention is a melting point determined in accordance with the method in ASTM D3418. The heat deformation temperature (deflection temperature under load) in the present invention is a heat deformation temperature (deflection temperature under load) determined in accordance with the method in ISO 75.

The medical tube of the present invention is thin-walled and flexible, has excellent kink resistance and tensile strength, and can be easily joined to a member such as another tube. Therefore, the medical tube is widely applicable to a medical device such as a catheter. The medical tube is applicable to not only the hand shaft and the leading end shaft of a catheter as described above but also medical devices using a guide wire lumen or other tubes. For example, when the medical tube is used as a shaft of a balloon catheter, the deflation time of a balloon can be reduced because the shaft obtains a small wall thickness, thereby having a large inner cavity. When the medical tube is used as a shaft of a catheter for injecting a medicinal agent, the injection amount of a medicinal agent can be increased because the shaft obtains a small wall thickness, thereby having a large inner cavity. When the medical tube is used as a shaft of a catheter for aspirating a blood clot, the aspiration amount of a blood clot can be increased because the shaft obtains a small wall thickness, thereby having a large inner cavity. When the medical tube is used as a shaft of a catheter for delivering another catheter, a larger catheter or the like can be delivered because the shaft obtains a small wall thickness, thereby having a large inner cavity. When the catheter has a similar inner cavity to that of a conventional catheter, the catheter obtains a smaller outer diameter, thereby enabling more minimally invasive treatment and treatment in a thinner peripheral lumen in the body.

When the medical tube of the present invention is applied to such a catheter, the medical tube may further include an inner layer in the inner cavity of the coil layer, for example, in order to make the inner cavity of the medical tube smooth. In particular, when the wound shape of a coil is a pitch wound shape, such an inner layer enables a guide wire or another catheter to more smoothly pass through the inner cavity of the medical tube. However, in order to reduce the wall thickness of a medical tube, the wall thicknesses of the inner layer, the outer layer tube, the coil layer, the intermediate layer provided as necessary, and the second outer layer provided as necessary may be appropriately designed considering the kink resistance and the tensile strength of a medical tube obtained by the manufacturing method of the present invention.

EXAMPLES

Hereinafter, the present invention will be described in further detail with reference to examples, but the present invention is not intended to be limited to these examples. The examples below show the comparison of kink resistance, tensile strength, and tensile elongation and do not describe the possibility of reducing wall thickness and easiness of production.

Example 1

A coil layer used was a tightly wound coil having an inner diameter of 1.00 mm and a length of 300 mm and made of a stainless steel flat wire (a thickness of 0.10 mm, a width of 0.20 mm). An outer layer tube used was a polyurethane elastomer (a Shore D hardness of 68 D, a melting point of 182° C.) tube that had an inner diameter of 1.25 mm and an outer diameter of 1.39 mm and was prepared using an extruder through extrusion molding by common pulling down while injecting air into an inner cavity.

Into the inner cavity of the prepared coil, a stainless steel core material having a diameter of 0.98 mm and a length of 400 mm was inserted, and the whole was inserted into the outer layer tube. The whole in this state was heated in an oven adjusted at 130° C. for 2 minutes. After taking out from the oven, the stainless steel core material was pulled out, thereby affording a medical tube having an inner diameter of 1.00 mm, an outer diameter of 1.35 mm, and a length of 300 mm.

Example 2

A coil layer used was a pitch wound coil having an inner diameter of 1.00 mm, a clearance between wires of 0.05 mm (a pitch of 0.15 mm), and a length of 300 mm and made of a stainless steel flat wire (a thickness of 0.02 mm, a width 0.10 mm). An outer layer tube and an intermediate layer used were a two-layer tube that had an inner diameter of 1.08 mm, an outer diameter of 1.20 mm, and a length of 300 mm, included an outer layer (outer layer tube) having a thickness of 0.05 mm and made of a polyurethane elastomer (a Shore D hardness of 68 D, a melting point of 182° C.) and an inner layer (intermediate layer) having a thickness of 0.01 mm and made of a polyurethane elastomer (a Shore A hardness of 85 A, a melting point of 163° C.), and was prepared using an extruder through extrusion molding of two-layer tube by common pulling down while injecting air into an inner cavity.

Into the inner cavity of the prepared coil, a stainless steel core material having a diameter of 0.98 mm and a length of 400 mm was inserted, and the whole was inserted into the two-layer tube. The whole in this state was heated in an oven adjusted at 130° C. for 2 minutes. After taking out from the oven, the stainless steel core material was pulled out, thereby affording a medical tube having an inner diameter of 1.00 mm, an outer diameter of 1.16 mm, and a length of 300 mm.

Example 3

A coil layer was the same as in Example 1. An outer layer tube used was a polyamide elastomer (a Shore D hardness of 72 D, a melting point of 176° C., a heat deformation temperature of 106° C.) tube that had an inner diameter of 1.25 mm and an outer diameter of 1.39 mm and was prepared using an extruder through extrusion molding by common pulling down while injecting air into an inner cavity.

Into the inner cavity of the prepared coil, a stainless steel core material having a diameter of 0.98 mm and a length of 400 mm was inserted, and the whole was inserted into the outer layer tube. The whole in this state was heated in an oven adjusted at 130° C. for 2 minutes. After taking out from the oven, the stainless steel core material was pulled out, thereby affording a medical tube having an inner diameter of 1.00 mm, an outer diameter of 1.35 mm, and a length of 300 mm.

Example 4

A coil layer and an outer layer tube were the same as in Example 1.

Into the inner cavity of the prepared coil, a stainless steel core material having a diameter of 0.98 mm and a length of 400 mm was inserted, and the whole was inserted into the outer layer tube. Then, a heat shrinkable tube (made of polyolefin, a shrinkage temperature of 115° C. or more, a shrinkage ratio of 40% or more, an inner diameter of about 1.5 mm) was applied on the outside of the outer layer tube over the entire length, and the whole was heated in an oven adjusted at 174° C. for 2 minutes. After taking out from the oven, the heat shrinkable tube was peeled and the stainless steel core material was pulled out, thereby affording a medical tube having an inner diameter of 1.00 mm, an outer diameter of 1.35 mm, and a length of 300 mm.

Example 5

A coil layer and an outer layer tube were the same as in Example 3.

Into the inner cavity of the prepared coil, a stainless steel core material having a diameter of 0.98 mm and a length of 400 mm was inserted, and the whole was inserted into the outer layer tube. Then, a heat shrinkable tube (made of polyolefin, a shrinkage temperature of 115° C. or more, a shrinkage ratio of 40% or more, an inner diameter of about 1.5 mm) was applied on the outside of the outer layer tube over the entire length, and the whole was heated in an oven adjusted at 170° C. for 2 minutes. After taking out from the oven, the heat shrinkable tube was peeled and the stainless steel core material was pulled out, thereby affording a medical tube having an inner diameter of 1.00 mm, an outer diameter of 1.35 mm, and a length of 300 mm.

Example 6

A coil layer was the same as in Example 2. An outer layer tube and an intermediate layer used were a two-layer tube that had an inner diameter of 1.08 mm, an outer diameter of 1.20 mm, and a length of 300 mm, included an outer layer (outer layer tube) having a thickness of 0.05 mm and made of a polyamide elastomer (a Shore D hardness of 70 D, a melting point of 174° C., a heat deformation temperature of 99° C.) and an inner layer (intermediate layer) having a thickness of 0.01 mm and made of a polyamide elastomer (a Shore D hardness of 35 D, a melting point of 152° C., a heat deformation temperature of 46° C.), and was prepared using an extruder through extrusion molding of two-layer tube by common pulling down while injecting air into an inner cavity.

Into the inner cavity of the prepared coil, a stainless steel core material having a diameter of 0.98 mm and a length of 400 mm was inserted, and the whole was inserted into the two-layer tube. Then, a heat shrinkable tube (made of polyolefin, a shrinkage temperature of 115° C. or more, a shrinkage ratio of 40% or more, an inner diameter of about 1.5 mm) was applied on the outside of the two-layer tube over the entire length, and the whole was heated in an oven adjusted at 170° C. for 2 minutes. After taking out from the oven, the heat shrinkable tube was peeled and the stainless steel core material was pulled out, thereby affording a medical tube having an inner diameter of 1.00 mm, an outer diameter of 1.16 mm, and a length of 300 mm.

Example 7

A coil layer and an outer layer tube were the same as in Example 3.

Into the inner cavity of the prepared coil, a stainless steel core material having a diameter of 0.98 mm and a length of 400 mm was inserted, and the whole was inserted into the outer layer tube. One end of the outer layer tube was passed through a stainless steel die (an inner diameter of 1.35 mm). The die was heated at 170° C., and then one end of the outer layer tube passed through the die was pulled at a constant speed, thereby pulling the entire length of the coil layer and the outer layer tube out of the die. Then, the stainless steel core material was pulled out, thereby affording a medical tube having an inner diameter of 1.00 mm, an outer diameter of 1.35 mm, and a length of 300 mm.

Example 8

A coil layer was the same as in Example 2. An outer layer tube and a second outer layer used were a two-layer tube that had an inner diameter of 1.08 mm, an outer diameter of 1.22 mm, and a length of 300 mm, included an outer layer (second outer layer) having a thickness of 0.02 mm and made of a polyamide elastomer (a Shore D hardness of 35 D, a melting point of 152° C., a heat deformation temperature of 46° C.) and an inner layer (outer layer tube) having a thickness of 0.05 mm and made of a polyamide elastomer (a Shore D hardness of 70 D, a melting point of 174° C., a heat deformation temperature of 99° C.), and was prepared using an extruder through extrusion molding of two-layer tube by common pulling down while injecting air into an inner cavity.

Into the inner cavity of the prepared coil, a stainless steel core material having a diameter of 0.98 mm and a length of 400 mm was inserted, and the whole was inserted into the two-layer tube. Then, a heat shrinkable tube (made of polyolefin, a shrinkage temperature of 115° C. or more, a shrinkage ratio of 40% or more, an inner diameter of about 1.5 mm) was applied on the outside of the two-layer tube over the entire length, and the whole was heated in an oven adjusted at 170° C. for 2 minutes. After taking out from the oven, the heat shrinkable tube was peeled, thereby affording a medical tube having an inner diameter of 1.00 mm, an outer diameter of 1.18 mm, a length of 300 mm and including the stainless steel core material.

A second tube (an inner diameter of 0.41 mm, an outer diameter of 0.56 mm, a length of 150 mm) that was made of a polyamide elastomer (a Shore D hardness of 55 D, a melting point of 168° C., a heat deformation temperature of 66° C.) and into which a stainless steel core material having a diameter of 0.40 mm was inserted was disposed along and parallel to the medical tube including the stainless steel core material, in a range of 150 mm from one end of the medical tube. A heat shrinkable tube (made of polyolefin, a shrinkage temperature of 115° C. or more, a shrinkage ratio of 40% or more, an inner diameter of about 2.0 mm) was applied so as to include both the medical tube including the stainless steel core material and the second tube including the stainless steel core material, and the whole was heated in an oven adjusted at 170° C. for 2 minutes. After taking out from the oven, the heat shrinkable tube was peeled, and the stainless steel core material having a diameter of 1.00 mm and the stainless steel core material having a diameter of 0.40 mm were pulled out, thereby affording a medical assembly that had a length of 300 mm and included a part welded with the second tube in parallel having a length of 150 mm and a part with the medical tube alone having a length of 150 mm.

Comparative Example 1

A medical tube was obtained in the same manner as in Example 4 except that the oven temperature was adjusted at 200° C.

Comparative Example 2

A medical tube was obtained in the same manner as in Example 5 except that the oven temperature was adjusted at 200° C.

Comparative Example 3

A medical tube was obtained in the same manner as in Example 6 except that the oven temperature was adjusted at 200° C.

Comparative Example 4

A coil layer was the same as in Example 1. An outer layer tube used was a polyurethane elastomer (a Shore D hardness of 68 D) tube that had an inner diameter of 1.21 mm, an outer diameter of 1.35 mm, and a length of 300 mm and was prepared using an extruder through extrusion molding by common pulling down while injecting air into an inner cavity.

The prepared coil was elongated in the axial direction, then was twisted so as to reduce the outer diameter, and was inserted into the outer layer tube. The coil was returned to the original shape, thereby affording a medical tube having an inner diameter of 1.00 mm, an outer diameter of 1.35 mm, and a length of 300 mm.

Comparative Example 5

An outer layer tube used was a polyamide elastomer (a Shore D hardness of 72 D) tube that had an inner diameter of 1.21 mm, an outer diameter of 1.35 mm, and a length of 300 mm and was prepared using an extruder through extrusion molding by common pulling down while injecting air into an inner cavity. A medical tube was obtained in the same manner as in Comparative Example 4 except the outer layer tube.
(Evaluation)

Two evaluations by "kink resistance test" and "tensile test" were carried out as follows. In the evaluation by the "kink resistance test", in a similar movement of operating a catheter or the like to that in a clinical practice, a medical tube was held at two sites and the held parts were brought close to each other, thereby bending the tube. In the evaluation by the "tensile test", in a similar movement of pulling a catheter or the like to that in a clinical practice, a medical tube was held at two sites and the held medical tube was pulled. Each medical tube manufactured in Examples 1 to 8 and Comparative Examples 1 to 5 was evaluated by two tests, and for the medical tube manufactured in Example 8 alone, a part joined with the second tube was also evaluated by the same tests.
(Kink Resistance Test)

The medical tube was set in a straight position. Two sites spaced apart a predetermined distance from each other in the longitudinal direction were held by right and left hands. Both hands were slowly brought close to each other along a straight line until the distance between the held sites reached 10 mm, thereby bending the medical tube. At the time when the distance reached 10 mm, the presence or absence of kink was observed. Here, the kink means a state in which cracking, folding, or large plastic deformation (for example, elongation) has been caused in the outer layer tube, and such a tube is unlikely to be returned to the original medical tube even when the tube is returned to a straight position. Two initial holding distances of 70 mm and 50 mm were designed. At the holding distance of 70 mm, the tube was extremely highly bent when the test was carried out to the last. The holding distance of 50 mm led to a harsher condition. As the evaluation result, a tube that was not kinked in each condition is represented by A, a tube that was not kinked at 70 mm but was kinked at 50 mm is represented by B, and a tube that was kinked at 70 mm is represented by C, thereby evaluating the kink resistance of each medical tube.

The results of the kink resistance test are shown in Table 1.

TABLE 1

|  |  | Kink resistance | Breaking mode |
|---|---|---|---|
| Example 1 |  | B | — |
| Example 2 |  | B | — |
| Example 3 |  | B | — |
| Example 4 |  | A | — |
| Example 5 |  | A | — |
| Example 6 |  | A | — |
| Example 7 |  | A | — |
| Example 8 | Tube alone | A | — |
|  | Assembly | A | — |
| Comparative Example 1 |  | C | Outer layer cracked |
| Comparative Example 2 |  | C | Outer layer cracked |
| Comparative Example 3 |  | C | Outer layer cracked |

TABLE 1-continued

|  | Kink resistance | Breaking mode |
|---|---|---|
| Comparative Example 4 | C | Outer layer kinked |
|  |  | Coil displaced and overlapped |
| Comparative Example 5 | C | Outer layer kinked |
|  |  | Coil displaced and overlapped |

Each medical tube of Examples 1 to 3 was not kinked to the last in the test with a holding distance of 70 mm, did not cause crushing of the inner cavity, cracking of the outer layer, and displacement of the coil, and showed fine kink resistance. In the test with a holding distance of 50 mm, the reduction in load was sensed when the sites were brought close to a distance of 20 mm, and thus the medical tube was judged to be kinked. However, when the medical tube was returned to a straight position, the displacement and overlapping of the coil were not observed and the medical tube was returned to a state of the original medical tube.

Each medical tube of Examples 4 to 8 was not kinked to the last in each of the test with a holding distance of 70 mm and the test with a holding distance of 50 mm, did not cause crushing of the inner cavity, cracking of the outer layer, and displacement of the coil, and showed fine kink resistance. In Example 8, the medical assembly joined with the second tube also showed fine kink resistance.

In each medical tube of Comparative Examples 1 to 2, the outer layer tube was cracked and the tube was kinked when the sites were brought close to a distance of 20 mm in the test with a holding distance of 70 mm.

In the medical tube of Comparative Example 3, the outer layer tube was elongated at a clearance between wires of the coil and the tube was kinked when the sites were brought close to a distance of 20 mm in the test with a holding distance of 70 mm. Even when the medical tube was returned to a straight position, the area at which the outer layer tube was elongated was still loose. The rigidity of the medical tube was extremely reduced and the outer diameter was increased.

In each medical tube of Comparative Examples 4 to 5, the outer layer tube was kinked, the coil was displaced and overlapped, and the medical tube was kinked when the sites were brought close to a distance of 40 mm in the test with a holding distance of 70 mm. Even when the medical tube was returned to a straight position, the displacement and the overlapping of the coil were not eliminated.

(Tensile Test)

The tensile test of each medical tube was carried out using a tension and compression testing machine (Shimadzu Corporation) in a condition at a chuck distance of 50 mm and a tension rate of 1,000 mm/min, and the tensile strength and the tensile elongation were evaluated. The tensile strength and the tensile elongation were a maximum load and a maximum displacement when a part except the coil of the medical tube including a coil layer was broken. The tensile elongation was represented by (displacement when a tube is broken/chuck distance)×100[%]. Here, the displacement when a tube is broken means a distance when a tube is broken where the distance chucked is 0 mm, and is an actually elongated distance of a medical tube.

The results of the tensile test are shown in Table 2.

TABLE 2

|  |  | Tensile test | |
|---|---|---|---|
|  |  | Tensile strength [N] | Tensile elongation [mm] |
| Example 1 | | 16 | 222 |
| Example 2 | | 12 | 119 |
| Example 3 | | 18 | 240 |
| Example 4 | | 16 | 210 |
| Example 5 | | 18 | 228 |
| Example 6 | | 12 | 108 |
| Example 7 | | 18 | 220 |
| Example 8 | Tube alone | 14 | 123 |
|  | Assembly | 15 | 141 |
| Comparative Example 1 | | 8 | 191 |
| Comparative Example 2 | | 9 | 217 |
| Comparative Example 3 | | 5 | 31 |
| Comparative Example 4 | | 15 | 240 |
| Comparative Example 5 | | 17 | 251 |

The tensile strength of each medical tube of Examples 1 to 8 varied depending on the hardness of a resin and the wall thickness of an outer layer tube, but each medical tube showed an enough tensile strength of 12 to 18 N. Each tensile elongation also varied as with the tensile strength but was 108 to 240% that was twice or more elongation than the initial state. In Example 8, the medical assembly joined with the second tube also showed a tensile strength of 15 N and a tensile elongation of 141% that were substantially the same results as those of the medical tube.

The tensile strength of each medical tube of Comparative Examples 4 to 5 varied depending on the hardness of a resin and the wall thickness of an outer layer tube, but each medical tube showed an enough tensile strength of 15 to 17 N. Each tensile elongation also varied as with the tensile strength but was 240 to 251% that was twice or more elongation than the initial state.

The tensile strength of each medical tube of Comparative Examples 1 to 3 varied depending on the hardness of a resin and the wall thickness of an outer layer tube, but each medical tube was broken at a low load of 5 to 9 N. The tensile elongation of each medical tube of Comparative Examples 1 to 2 was 191 to 217% that was twice or more elongation than the initial state. However, the medical tube of Comparative Example 3 had a tensile elongation of 31% and was broken soon after the start of elongation.

From the results, it was ascertained that each medical tube of Examples 1 to 3 was not kinked even when the tube was very highly bent, and caused the sense of kink in a harsher condition, but could be used again as a medical tube by returning the medical tube to a straight position. With regard to the tensile strength and the tensile elongation, each medical tube also showed enough load and enough elongation, and it was ascertained that each medical tube could be safely used as a medical tube.

It was ascertained that each medical tube of Examples 4 to 8 was not kinked even in an extremely harsh condition and could be used as a medical tube. With regard to the tensile strength and the tensile elongation, each medical tube also showed enough load and enough elongation, and it was ascertained that each medical tube could be safely used as a medical tube. In Example 8, it was ascertained that the medical tube could also be safely used as a medical assembly.

It was ascertained that each medical tube of Comparative Examples 1 to 3 underwent cracking and kinking of the outer layer tube when the medical tube was highly bent and could not be used as a medical tube. With regard to the tensile strength, each tube was broken at a low load. In particular, the medical tube of Comparative Example 3 was broken at a small tensile elongation. It was ascertained that each medical tube of Comparative Examples 1 to 3 had safety concerns as a medical tube.

With regard to the tensile strength and the tensile elongation, each medical tube of Comparative Examples 4 to 5 showed an enough load and an enough elongation because each medical tube was merely a resin tube. However, the outer layer tube was kinked and the coil was displaced and overlapped when the tube was highly bent. Therefore, it was ascertained that each tube could not be used as a medical tube.

REFERENCE SIGNS LIST

101, 201 Medical tube
102, 202 Outer layer tube
103, 203 Coil layer
104A Part in contact with a coil wire edge at the inside of the outer layer tube 102
104B Part in contact with a coil wire edge at the inside of the outer layer tube 102
105 Concave part
204 Intermediate layer
205 Between wires

The invention claimed is:

1. A method for manufacturing a medical tube, the medical tube including a coil layer on an inside of an outer layer tube made of a resin, the method comprising:
   inserting the coil layer into the outer layer tube; and
   heating the outer layer tube at a molding temperature lower than a melting point of the outer layer tube, thereby bringing the outer layer tube into contact with the coil layer to slidably fix the outer layer tube onto the coil layer, wherein
   the outer layer tube comprises a thermoplastic elastomer, and
   the outer layer tube has an inner diameter shrinkage ratio of 1% or more and 10% or less during the heating at the molding temperature.

2. A method for manufacturing a medical tube, the medical tube including an intermediate layer on an inside of an outer layer tube made of a resin and further including a coil layer on an inside of the intermediate layer, the method comprising:
   disposing the intermediate layer and the coil layer in the outer layer tube; and
   heating the outer layer tube at a molding temperature lower than a melting point of the outer layer tube, thereby slidably fixing the outer layer tube onto the coil layer through the intermediate layer, wherein
   the outer layer tube comprises a thermoplastic elastomer, and
   the outer layer tube has an inner diameter shrinkage ratio of 1% or more and 10% or less during the heating at the molding temperature.

3. The method for manufacturing a medical tube according to claim 1, wherein an external force is applied to reduce the inner diameter of the outer layer tube during the heating at the molding temperature.

4. The method for manufacturing a medical tube according to claim 3, wherein the external force is applied by disposing a heat shrinkable tube on an outside of the outer layer tube and the heat shrinkable tube has an inner diameter capable of being shrunk.

5. The method for manufacturing a medical tube according to claim 3, wherein the external force is applied by a mold from an outside of the outer layer tube.

6. The method for manufacturing a medical tube according to claim 3, wherein the external force is applied by pulling the outer layer tube out of a die.

7. The method for manufacturing a medical tube according to claim 3, wherein the external force is applied by elongating the outer layer tube.

8. The method for manufacturing a medical tube according to claim 1, wherein the coil layer includes a metal wire.

9. The method for manufacturing a medical tube according to claim 1, wherein the coil layer includes a wire having a flat shape.

10. The method for manufacturing a medical tube according to claim 1, wherein the coil layer is a tightly wound coil.

11. The method for manufacturing a medical tube according to claim 1, wherein the coil layer is a pitch wound coil.

12. The method for manufacturing a medical tube according to claim 2, wherein the intermediate layer includes a material having a higher flexibility than that of a material of the outer layer tube.

13. The method for manufacturing a medical tube according to claim 2, wherein the intermediate layer includes a material having a melting point lower than that of the outer layer tube.

14. The method for manufacturing a medical tube according to claim 2, wherein the molding temperature is higher than a melting point of a material constituting the intermediate layer.

15. The method for manufacturing a medical tube according to claim 2, wherein the outer layer tube and the intermediate layer are a two-layer tube before applying the outer layer tube and the intermediate layer onto the coil layer.

16. The method for manufacturing a medical tube according to claim 2, wherein the material of the intermediate layer is the same type as the material of the outer layer tube.

17. The method for manufacturing a medical tube according to claim 1, wherein a second outer layer is provided on the outside of the outer layer tube and the second outer layer includes a material having a melting point lower than that of the outer layer tube.

18. A method for manufacturing a medical tube, the medical tube including a coil layer on an inside of an outer layer tube made of a resin, the method comprising:

inserting the coil layer into the outer layer tube; and heating the outer layer tube at a molding temperature lower than a melting point of the outer layer tube, so that i) the outer layer tube shrinks and comes into contact with the coil layer and ii) the outer layer tube is slidably fixed onto the coil layer, wherein the outer layer tube comprises a thermoplastic elastomer, and the outer layer tube has an inner diameter shrinkage ratio of 1% or more and 10% or less during the heating at the molding temperature.

* * * * *